United States Patent [19]

Abraham et al.

[11] Patent Number: 5,344,994
[45] Date of Patent: Sep. 6, 1994

[54] PROCESS FOR THE PREPARATION OF CONIFERYL ALDEHYDE

[75] Inventors: Wolf-Rainer Abraham, Hillerse; Hans-Adolf Arfmann, Braunschweig, both of Fed. Rep. of Germany

[73] Assignee: Haarmann & Reimer GmbH, Holzminden, Fed. Rep. of Germany

[21] Appl. No.: 76,296

[22] Filed: Jun. 11, 1993

[30] Foreign Application Priority Data

Jun. 17, 1992 [DE] Fed. Rep. of Germany ....... 4219770

[51] Int. Cl.$^5$ ............................................. C07C 45/00
[52] U.S. Cl. ................................. 568/449; 435/149; 435/155; 435/156

[58] Field of Search ............... 568/449; 435/147, 155, 435/156, 830

[56] References Cited

U.S. PATENT DOCUMENTS 4,874,701 10/1989 Cooper ................................. 435/147
4,981,795 1/1991 Cooper ................................. 435/147

FOREIGN PATENT DOCUMENTS 3604874 8/1987 Fed. Rep. of Germany ...... 435/147

Primary Examiner—Werren B. Lone
Attorney, Agent, or Firm—Sprung Horn Kramer & Woods

[57] ABSTRACT

Coniferyl aldehyde can be prepared from eugenol with the aid of fungi or their constituents.

6 Claims, No Drawings

PROCESS FOR THE PREPARATION OF CONIFERYL ALDEHYDE

The invention relates to a process for the preparation of coniferyl aldehyde from eugenol with the aid of microorganisms or their constituents:

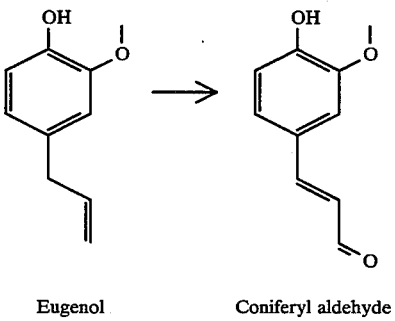

Eugenol      Coniferyl aldehyde

Coniferyl aldehyde has interesting organoleptic properties. Moreover, it has not been accessible to date in economical quantities. DE-OS 3,604,874 describes a process for the preparation of coniferyl aldehyde from eugenol with the aid of mutants of Arthrobacter globiformis DSM 3597. The corresponding mutants themselves have not been deposited, nor does DE-OS 3,604,874 contain a description of a reproducible process for obtaining them. This means that the disclosure is insufficient.

It has now been found that coniferyl aldehyde can be prepared in good yields from eugenol in the presence of fungi or their constituents.

The invention therefore relates to a process for the preparation of coniferyl aldehyde from eugenol, in which eugenol is combined with fungi or their constituents, the mixture is allowed to react, and the coniferyl aldehyde formed is separated off.

Preferred fungi include Ascomycetes, Fungi imperfecti and Phycomycetes.

Preferred Ascomycetes include the genera Gibberella (for example G. baccata, G. cyanea, G. fujikuroi, G. sanbinetti and G. zeae, for example IFO 5269), Chaetomium (for example Ch. cochlioides such as ATCC 10 195, Ch. funicolum, Ch. globosum, Ch. species and Ch. succineum), Cochliobolus (for example C. miyabeanus), Glomerella (for example G. cingulata, G. fluctigena, G. fusaroides, G. glycines, G. gossypii, G. lagenarium, G. major, G. mume, G. phacidiomorpha and G. rubicola)

Preferred Fungi imperfecti include the genera Aspergillus (for example A. aculeatus, A. alliaceus, A. amstelodami, A. asperescens, A. astianus, A. atropurpureus, A. aureus, A. auricomus, A. avenaceus, A. awamori, A. batatae, A. brevipes, A. butyracea, A. caesiellus, A. caespitosus, A. candidus, A. carbonarius, A. carneus, A. chevalieri, A. cinnamomeus, A. citri, A. citrisporus, A. clavatus, A. conicus, A. echinulatus, A. effusus, A. elegans, A. fischeri, A. flavipes, A. flavus, A. fonsecaeus, A. fumigatus, A. giganteus, A. glaucus, A. gracilis, A. gymnosardae, A. herbariorum, A. inuii, A. itaconicus, A. janus, A. japonicus, A. kanagawaensis, A. kawachii, A. lucheunsis, A. mangini, A. melleus, A. minimus, A. miyakoensis, A. mollis, A. montevidensis, A. nakazawai, A. nidulans, A. niger, for example ATCC 9142, A. niveo-glaucus, A. niveus, A. ochraceus, A. oryzae, A. ostianus, A. panamensis, A. parasiticus, A. penicilloides, A. phoenicis, A. proliferans, A. pseudoglaucus, A. pulverulentus, A. quadrilineatus, A. rehmii, A. repens, A. restrictus, A. ruber, A. rugulosus, A. saitoi, A. sclerotiorum, A. sojae, A. sparsus, A. species, A. sulphureus, A. sydowi, A. tamarii, A. terreus, A. terricola, A. unguis, A. usamii, A. ustus, A. varians, A. variecolor, A. versicolor, A. violaceofuscus and A. wentii), Beauveria (for example B. bassiana and B. species), Botryodiplodia (for example B. theobromae), Cercospora (for example C. apii, C. baticola, C. calotropidis, C. canescens, C. chenopodii, C. cladosporioides, C. cruenta, C. diazu, C. fusca, C. hibscicannabini, C. italica, C. kaki, C. kikuchii, C. lagenarum, C. macrospora, C. malvacearum, C. medicaginis, C. melongenae, C. melonis, C. musae, C. musarum, C. nicotianae, C. oryzae, C. rosicola, C. scirpicola, C. sesami, C. taiwanensis, C. vaginae, C. violae, C. zebrina and C. zinniae), Corynespora (for example C. casaiicoli, for example DSM 62 474), Curvularia (for example C. brachyspora, C. falcata, C. fallax, C. geniculata, C. inaequalis, C. lunata, C. maculans, C. oryzae, C. pallescens, for example DSM 62 482, C. species, C. tetramera, C. trifolii and C. uncinata), Gliocladium (for example G. catenulatum, G. deliquescens, G. luteolum, G. roseum and G. species), Diplodia (for example D. gossypina, for example ATCC 10 936, D. natalensis and D. tubericola), Fusarium (for example F. aquaeductum, F. arthoceras, F. aspidioti, F. avenaceum, F. batatatis, F. bulbigenum, F. buxicola, F. caucasicum, F. cocophilum, F. coeruleum, F. concolor, F. culmorum, F. dimerum, F. diversisporum, F. equiseti, F. expansum, F. fujikuroi, for example DSM 893, ATCC 12 764 and ATCC 14 842, F. gibosum, F. gigas, F. graminearum, for example DSM 62 722, F. herberum, F. heterosporum, F. inflexum, for example DSM 63 203, F. javanicum, F. lateritium, F. lini, F. lycopersici, F. macroceras, F. merismoides, F. microcrea, F. moniliforme, for example DSM 840, DSM 764 and DSM 768, F. nivale, F. niveum, F. niveus, F. orthoceras, F. oxysporum, for example ATCC 7601, F. oxysporum f. sp. achmeae, for example DSM 62 297, oxysporum f. sp. pisi, for example ATCC 9991, F. poae, F. pruni, F. redolens, F. reticulatum, for example DSM 62 719, F. roseum, for example DSM 3019, F. sambucinum, F. sarcochroum, F. semitectum, F. solani, for example DSM 62 413, DSM 1164 and DSM 62 416, F. species, F. sphaeriae, F. sporotrichella, F. sporotrichioides, F. sulphureum, F. tabacinum, for example DSM 2125, F. udum and F. vasinfectum), Penicillium (for example P. aculeatum, P. adametzi, P. albidum, P. asperum, P. atramentosum, P. arvense, for example CBS 513.74, P. aurantio-violaceum, P. aurantio-virens, P. avellaneum, P. biforme, P. brefeldianum, P. brevicompactum, P. camemberti, for example ATCC 4845, P. canescens, P. casei, P. caseicolum, P. charlesii, P. chermesinum, P. chrysogenum, P. citreoviride, P. citrinum, P. claviforme, P. clavigerum, P. commune, P. corylophilum, P. corymbiferum, P. crustosum, P. cyaneofulvum, P. cyaneum, P. cyclopium, P. daleae, P. decumbens, P. digitatum, for example DSM 62 840, P. diversum, for example CBS 320.48, P. duponti, P. egyptaceum, P. ehrlichii, P. expansum, P. fellutanum, P. frequentans, P. funiculosum, P. fuscum, P. gladioli, P. godlewskii, P. granulatum, P. helicum, P. herquei, P. humuli, P. implicatum, P. islandicum, P. italicum, P. janthinellum, P. javanicum, P. jensenii, P. kapuscinskii, P. lanosocoeruleum, P. lanoso-griseum, P. lanoso-viridi, P. lanesum, P. lavendulum, P. levitum, P. lilacinum, P. lividum, P. luteum, P. martensii, P. melearginum, P. melinii, P. micznskii, P. multicolor, P. nalgiovensis, P. namyslowskii, P. nigricans, P. notatum, P. novae-zeelandii, P. ochraceum, P. ochro-chlorum, P. olivino-viride, P. oxalicum, P. palitans, P. pallidum, P. parvum, P. patulum, P. phoenicum,

*P. piscarium, P. psittacinum, P. puberulum, P. pulvillorum, P. purpurescens, P. purpurogenum, P. pusilium, P. raciborskii, P. raistrickii, P. restrictum, P. restriculosum, P. rolfsii, P. roqueforti, P. roseo-purpureum, P. rubrum, P. rugulosum, P. sclerotiorum, P. simplicissimum, P. solitum, P. soppi,* P. species, *P. spiculisporum, P. spinulosum, P. steckii, P. stoloniferum, P. striatum, P. subalteritium, P. tardum, P. terlikowski, P. terrestre, P. thomii, P. trzebinskii, P. turbatum, P. urticae, P. variabile, P. vermiculatum, p. verruculosum,* for example ATCC 10 483, *P. vinaceum, P. viridicatum, P. waksmanni* and *P. wortmanni*) and Stachybotrys (for example St. species).

The preferred Phycomycetes include the genera Absidia (for example *A. coerulea,* for example ATCC 8990, *A. cylindrospora, A. glauca, A. hyalospora, A. orchidis, A. ramosa, A. regnieri, A. repens* and A. species), Cunninghamella (for example *C. africana, C. albidia, C. bainieri, C. blakesleeana, C. echinulata, C. elegans, C. homothallica, C. ramosa,* C. species and *C. verticillata*), Mortierella (for example *M. alpina, M. bainieri, M. candelabrum, M. isabellina, M. marburgensis, M. oligospora, M. polycephala, M. pusilla, M. tuberosa* and *M. zonata*), Mucor (for example *M. adriaticus, M. adventitius, M. angulisporus, M. berolinensis, M. buntingii, M. christianensis, M. circinelloides, M. circinelloides* f. *lusitanicus,* for example CBS 277.48, *M. corymbifer, M. dimorphosporus, M. dispersus, M. dubius, M. erectus, M. genevensis, M. globosus, M. glomerula, M. griseocyanus, M. guilliermondii, M. hiemalis, M. humicola, M. humilis, M. hypochninus, M. javanicus, M. mandshuricus, M. microsporus, M. mucedo, M. murorum, M. parasiticus, M. piriformis, M. plumbeus, M. pusillus, M. racemosus, M. ramannianus, M. rouxianus, M. rouxii, M. simplex, M. solani,* M. species, *M. sphaerospora, M. spinosus, M. stolonifer, M. varians* and *M. vuillemini*) as well as Rhizopus (for example *Rh. arrhizus, Rh. cambodjae, Rh. chinensis, Rh. chiuniang, Rh. cohnii, Rh. delemar, Rh. formosensis, Rh. japonicus, Rh. javanicus, Rh. kansho, Rh. kasanensis, Rh. nigricans, Rh. niveus, Rh. nodosus, Rh. oryzae, Rh. pseudochinensis, Rh. pygmaeus, Rh. reflexus, Rh. shangaiensis,* Rh. species, *Rh. stolonifer, Rh. suinus, Rh. tonkinensis* and *Rh. tritici*).

The fungi which are most preferred for the process according to the invention are those of the genus Fusarium; the most preferred species are *Fusarium moniliforme* such as, for example, DSM 840 and DSM 768, and *Fusarium fujikuroi* such as, for example, F. f. DSM 893. Equally preferred is the synonymous *Gibberella fujikuroi* (see J. C. Corell, Phytopathology 81 (1991), 1061–1064), for example ATCC 12 764 and ATCC 14 842.

In an embodiment of the process according to the invention, fungi are fermented in the presence of eugenol, and the resulting coniferyl aldehyde is isolated. It is also possible to employ, instead of the fungi, their constituents, i.e. their cell sap or the enzymes contained therein.

If the process according to the invention is carried out by fermenting fungi, it is advantageous to add a carbon source. Suitable carbon sources are, for example, aliphatic $C_6$–$C_{18}$-hydrocarbons, preferably $C_8$–$C_{14}$-hydrocarbons, such as, for example, n-hexane, n-octane, n-dodecane, the isomers of these compounds, the mixtures of the above-mentioned hydrocarbons including technical-grade mixtures, such as, for example, kerosene. The fermentation can take place with the carbon source as the medium.

It has proved advantageous to treat the culture with an inductor before the addition of eugenol. Examples of substances which act as inductors are: $C_1$–$C_{12}$-alkyl $C_2$–$C_{20}$-carboxylate such as butyl acetate and propyl oleate, substituted benzenes such as propylbenzene, allylbenzene, n-butylbenzene, 1,4-diethylbenzene, substituted phenols, unsubstituted and substituted phenol ethers such as, for example, 2-allyl-phenol, 2-allyl-6-methyl-phenol, 4-methoxy-3-hydroxystyrene, eugenol, isoeugenol, eugenol methyl ether and isoeugenol methyl ether, anisole, 4-vinylanisole and 4-allylanisole, phenetole, veratrole, veratryl alcohol, anethole, carvacrol, safrole, isosafrole, vanillyl alcohol, eugenol $C_2$–$C_{18}$-carboxylates and isoeugenol $C_2$–$C_{18}$-carboxylates such as, for example, eugenol acetate, eugenol butyrate, eugenol oleate, isoeugenol acetate, isoeugenol butyrate and isoeugenol oleate.

The starting material eugenol is generally employed in an amount of 0.1 to 20, preferably 0.3 to 3, g per 1 of culture broth. It can added in pure form or in the form of a solution. Organic solvents which can diluted with water such as, for example, ethanol or dimethylformamide, are preferred for preparing the eugenol solution.

The carbon source is generally employed in an amount of 0.2 to 200, preferably 0.5 to 20, g per 1 of culture broth. As a rule, the inductor is employed in an amount of 5 to 2000, preferably 10 to 500, mg per 1 of culture broth. If it is desired to use an inductor in the process, this is best done in such a way that the culture medium containing the fungal culture is induced by means of the inductor and the fungi are then cultured for 0.5 to 3 days. The eugenol can then be added. Alternatively, the mycelium can be separated off and used for the process according to the invention. If the mycelium is first digested, the cell debris is separated off and the eugenol is added to the cell-free extract, the result may be coniferyl alcohol, which can then be oxidised with the culture supernatant to give coniferyl aldehyde.

The progress of the reaction can be monitored by means thin-layer chromatography.

As a rule, work-up is effected in such a way that supernatant and mycelium are separated and extracted with organic solvent (for example ethyl acetate), the solvent is stripped off, and the residue is purified, for example by chromatography.

EXAMPLES

A preculture is prepared by first inoculating a 100 ml Erlenmeyer flask, containing 20 ml of sterilised culture medium comprising 10 g/l n-dodecane, 3 g/l sodium nitrate, 1 g/l yeast extract, 1.3 g/l $K_2HPO_4 \times 3\ H_2O$, 0.5 g/l KCl, 0.5 g/l $MgSO_4 \times 7\ H_2O$, 0.05 g/l $FeSO_4 \times 7\ H_2O$ and 0.7 g/l citric acid $\times 1\ H_2O$ and which has been brought to pH 4.5 prior to autoclaving, with a fully-grown agar slant culture of the suitable microorganisms and incubating the flask for 24 to 72 hours at 27° C. and 140 rpm. This culture is subsequently transferred under sterile conditions to a 1000 ml Erlenmeyer flask containing 200 ml of culture medium, simultaneously induced with a suitable inductor and cultured for 24 to 48 hours under the abovementioned conditions. The substrate, in pure form or dissolved in dimethylformamide or ethanol (50 mg/ml), is then added at a substrate concentration of 0.5 to 2 g/l. The course of the metabolisation is monitored by thin-layer chromatography. To this end, 1 ml of a sample which has been taken under sterile conditions is treated with 0.2 ml of ethyl acetate, and the mixture is shaken for 2 minutes and centrifuged for 2 minutes. 20 μl of supernatant are applied to HPTLC precoated plates, silica gel Si-60 (Merck), developed using n-hexane/ethyl acetate in a ratio of 6:4 by volume, viewed under UV (254 or 366 nm) and subsequently sprayed with anisaldehyde spray reagent (0.6 ml of anisaldehyde, 1.0 ml of sulphuric acid, 50 ml of acetic acid) and developed for 2 minutes at 100° C. In this way, the oxidation products are located as coloured spots.

For preparative work-up, supernatant and mycelium are separated and in each case extracted three times using ethyl acetate, the extracts are combined, and the solvent is stripped off in vacuo.

Separation by chromatography is effected using silica gel (Si 60, particle size 40 to 63 μm, Merck) using n-hexane/ethyl acetate run as a gradient. The starting ratio is 100:0 n-hexane/ethyl acetate, and the end ratio is 6:4 (ratios based on parts by volume).

Example 1

Diplodia gossypina ATCC 10936 is used for inoculating 800 ml of the abovementioned medium with n-dodecane as carbon source and, during inoculation, induced using 400 mg of eugenol oleate. The culture is allowed to grow for 3 days, after which 400 mg of eugenol are added. After a contact time of 143 hours, 45 mg of coniferyl aldehyde (10.4% of theory) as well as 100 mg of unmetabolised eugenol are isolated.

Example 2

If the procedure of Example 1 is followed, but 25 ppm of eugenol acetate are employed as inductor in place of eugenol oleate, and if the fungus Fusarium moniliforme DSM 764 is used, 252 mg of coniferyl aldehyde (58% of theory) are obtained.

Example 3

If the procedure of Example 1 is followed, but Fusarium moniliforme DSM 840 and eugenol methyl ether are employed at a concentration of 25 ppm, the induction time is 24 hours and the substrate concentration is increased to 2 g/l, 999 mg of coniferyl aldehyde (57.5% of theory) are obtained after 72 hours.

Example 4

If the procedure of Example 3 is followed but, after induction, the mycelium is removed by centrifugation and suspended in a phosphate buffer (pH 7.0) to which 2 g of eugenol are added, 991 mg of coniferyl aldehyde (45% of theory, 57.8% of the conversion) in addition to 420 mg of eugenol are obtained after 143 hours.

Example 5

If the procedure of Example 4 is followed, but the mycelium is digested, the cell debris is separated off and 2 g of eugenol are added to the cell-free extract, 910 mg of coniferyl alcohol are obtained after 24 hours. This coniferyl alcohol can be oxidised quantitatively using the culture supernatant to give coniferyl aldehyde.

We claim:

1. A process for preparing coniferyl aldehyde which comprises:
   combining 0.1 to 20 g/l of culture broth of eugenol with a fungus or its constituents wherein the fungus is selected from the group consisting of Ascomycetes, Fungi imperfecti, and Phycomycetes;
   fermenting the mixture optionally in the presence of a carbon source, and
   separating the coniferyl aldehyde from the fermentation mixture.

2. The process according to claim 1, in which the fungi used are of the genera Absidia, Aspergillus, Chaetomium, Corynespora, Curvularia, Diplodia, Gibberella, Fusarium, Mucor, or Penicillium.

3. The process according to claim 1, in which the fungi are selected from the group consisting of *Absidia coerulea, Aspergillus niger, Corynespora cassiicola, Curvularia pallescens, Chaetomium cochliodes, Diplodia gossypina, Fusarium graminearum, Fusarium fujikuroi, Fusarium inflexum, Fusarium moniliforme, Fusarium oxysporum, fusarium oxysporum f. sp. aechmeae, Fusarium oxysporum f. sp. pisi, fusarium reticulatum, Fusarium roseum, Fusarium solani, Fusarium tabacinum, Gibberella zeae, Mucor circinelloides f. lusitanicus, Penicillium arvense, Penicillium camemberti, Penicillium digitatum, Penicillium diversum*, and *Pencillium verruculosum*.

4. The process according to claim 1, in which the culture is treated with an inductor before the addition of eugenol.

5. The process according to claim 4, wherein the inductors are eugenol methyl esters, eugenol esters, safrole, isoeugenol, isoeugenol acetate, vanillyl alcohol, n-butylbenzene, or 4-allylanisole.

6. The process according to claim 5, wherein the eugenol esters are eugenol acetate and eugenol oleate.

* * * * *